US008147490B2

(12) United States Patent
Bauer

(10) Patent No.: US 8,147,490 B2
(45) Date of Patent: Apr. 3, 2012

(54) FIXATION DEVICE FOR STABLY INTERLINKING AT LEAST TWO BONE FRAGMENTS OF A BROKEN BONE AND CORRESPONDING FIXATION ELEMENT AND KIT

(75) Inventor: Eckhard Bauer, Schönberg (DE)

(73) Assignee: Tantum AG, Neumuenster (DE)

( * ) Notice: Subject to any disclaimer, the term of this patent is extended or adjusted under 35 U.S.C. 154(b) by 587 days.

(21) Appl. No.: 11/887,582

(22) PCT Filed: Mar. 28, 2006

(86) PCT No.: PCT/EP2006/002951
§ 371 (c)(1),
(2), (4) Date: Jun. 25, 2009

(87) PCT Pub. No.: WO2006/103087
PCT Pub. Date: Oct. 5, 2006

(65) Prior Publication Data
US 2009/0299368 A1    Dec. 3, 2009

(30) Foreign Application Priority Data
Apr. 1, 2005    (DE) .................... 20 2005 005 444 U

(51) Int. Cl.
*A61B 17/00*    (2006.01)
(52) U.S. Cl. ........................................ 606/57
(58) Field of Classification Search .............. 606/53–59
See application file for complete search history.

(56) References Cited
U.S. PATENT DOCUMENTS
4,483,334 A * 11/1984 Murray ........................ 606/59
4,600,000 A * 7/1986 Edwards ...................... 606/54
4,620,533 A * 11/1986 Mears .......................... 606/54
(Continued)

FOREIGN PATENT DOCUMENTS
| DE | 3611319 A1 | 10/1987 |
| DE | 29512917 U1 | 11/1995 |
| WO | WO-98/32385 | 7/1998 |
| WO | WO-03/034930 A1 | 5/2003 |

OTHER PUBLICATIONS
International Search Report dated Jul. 13, 2006, issued in PCT/EP2006/002951.
German Search Report From 20 2005 005 444.5 Dated January 12, 2005 With an English Translation.

*Primary Examiner* — Eduardo C Robert
*Assistant Examiner* — Stuart S Bray
(74) *Attorney, Agent, or Firm* — Venable LLP; Robert Kinberg

(57) ABSTRACT

A device to establish a connection of portions of a broken bone includes a base body adapted to receive a bone nail. A clamping holder has a receptacle to receive a fixation rod. A bearing element mounts the clamping holder on the base body for spherically displacement. A tensioning rod connection has a tensioning rod on which the base body, the clamping holder and the bearing element are arrangeable in a row for tensioning relative to each other. In a first connection state the tensioning rod connection is released so that the fixation rod and base body are adjustable relative to each other. In a second connection state there is sufficient closing tension in the tensioning rod connection to form a stable non-positive locking connection between the fixation rod and the base body. The clamping holder and the bearing element are in positive engagement in the first connection state with the tensioning rod passing through a through-opening of the clamping holder with sufficient play for spatial guiding in all directions.

25 Claims, 5 Drawing Sheets

U.S. PATENT DOCUMENTS

| | | | |
|---|---|---|---|
| 5,207,676 A * | 5/1993 | Canadell et al. | 606/54 |
| 5,312,402 A * | 5/1994 | Schlapfer et al. | 606/53 |
| 5,393,161 A * | 2/1995 | Mata et al. | 403/133 |
| 5,624,440 A * | 4/1997 | Huebner | 606/59 |
| 5,921,985 A * | 7/1999 | Ross et al. | 606/59 |
| 6,217,577 B1 * | 4/2001 | Hofmann | 606/57 |
| 6,482,206 B2 * | 11/2002 | Schoenefeld | 606/59 |
| 2002/0077629 A1 * | 6/2002 | Hoffman et al. | 606/59 |
| 2003/0109879 A1 | 6/2003 | Orsak | |
| 2010/0100096 A1 * | 4/2010 | Hollawell | 606/59 |

* cited by examiner

FIXATION DEVICE FOR STABLY INTERLINKING AT LEAST TWO BONE FRAGMENTS OF A BROKEN BONE AND CORRESPONDING FIXATION ELEMENT AND KIT

CROSS REFERENCE TO RELATED APPLICATION

The present application is a U.S. National Stage of International Application No. PCT/EP2006/002951, filed Jan. 19, 2007, designating the United States and claiming priority to German application DE 20 2005 005 444.5, filed Apr. 1, 2005.

BACKGROUND

The invention concerns a fixation device for the stable connection of at least two bone portions of a broken bone, including at least one base body for tightly receiving at least one bone nail, at least one fixation rod which can be connected to the base body by means of a clamping joint, base body and fixation rod being released in a first connection state of the fixation device for adjusting their relative position and rigidly connected to each other by non-positive locking in a second connection state for fixing the adjusted position, a clamping holder which is mounted with adjustable angle on the base body and which receives a fixation rod for altering and adjusting its position in a receptacle, a bearing which mounts the clamping holder on the base body, and a connection to a tensioning rod on which the base body, the rod clamping holder and the bearing for the clamping holder are arranged in a row for tensioning relative to each other, wherein on the one hand the released connection is made when the tensioning rod connection is released, and on the other hand the stable non-positive locking connection is made when there is sufficient closing tension in the tensioning rod connection, wherein the rod clamping holder is formed by a holder which spherically displaces the fixation rod and which is guided in all spatial directions in a region for displacing and maintaining the set position on the base body, wherein the clamping holder and at least one bearing element of the bearing connecting the clamping holder to the base body are in a positive engagement which produces the spatial guidance, the tensioning rod passing through the bearing element. The invention also relates to a fixation element of such a device and a kit receiving its components in a sterile package.

A generic device which is also referred to as a fixator serves to make a fixation connection between bone portions in order to treat fractures. In particular, such fixators are applied in the case of fractures of the radius involving the wrist. Bone nails introduced into the bone portions must be rigidly connected to at least one fixation rod in order to allow the bone portions to grow together in the correct position relative to each other. According to the arrangement and alignment of the bone nails and the area to be bridged, the fixation rod must be capable of being aligned. In the aligned position, it must be capable of rigid connection to the base bodies which in turn can be fixed to the bone nails in a stable rigid connection.

A number of requirements are made of the fixators. High stability must be guaranteed. Fixed bones must not change their position relative to each other even when the fixator is worn for several weeks. This requires high stability particularly in the connections of individual components. The fixator is to be capable of being handled easily in order to shorten the operation time. Also, it is to be relatively light in weight. The fixation device is also to be cheaply available. This is especially important particularly with a view to disposable use when this is worthwhile compared with treating the components for reuse. Thus fixators which should be used several times as a result of high purchase costs are frequently not returned after they are used, so that a loss is incurred as a result. Also, special procedures and measures are necessary particularly for sterilisation in case of reuse.

Known fixators do not meet the above requirements. Fixation elements of a generic fixator include a base body having a rod clamping bearing which is spherically displaceable for positioning a fixation rod, wherein parts of the fixation element are connected by means of a tensioning rod (U.S. Pat. No. 5,393,161 A). A clamping holder ball is encased in a hinge joint. Consequently the fixation element is bulky, and handling is made more difficult. For the construction of a fixation device, screw clamps for bone nails and screw connections for fixation rods are necessary in addition. Fixation elements known from US 2003/109879 A1 are displaceable in only two planes for positioning a fixation rod in a screw connection. For displacement in other planes, additional parts with additional screw connections are provided. Clamping elements are arranged on different bearing axes. Other clamping holder devices having several screw connections on different bearing axes are relatively hard to handle when they are released, they tend to become released in the tensioned state, and they are made with relatively heavy clamping parts from metal. Fixators according to US 2003/109879 A1 and other known fixators provide one screw connection each for a number of bone nails and fixation rods. With these devices, handling is made particularly difficult, as a result of the plurality of screw connections there is a susceptibility to instability, and relatively solid metal elements are used for the screw connections in order to increase the rigidity of the connection.

SUMMARY

It is the aim of the invention to design a fixation device in such a way that it is particularly easy to handle and cheaply available with relatively few components, wherein the rigidity of the connection can be guaranteed particularly high and reliable over a long period of time. Nevertheless it should be possible to make the components of the device from lightweight material and cheaply in mass production, in particular from plastic parts made by injection moulding. If necessary, manufacture should be so cheap that the product is usable as a cheap disposable product, in order to simplify the procedures in particular in a hospital by avoiding return, reprocessing and sterilisation of already used fixators.

The aims of the invention are achieved in conjunction with the features of the fixation device of the kind mentioned hereinbefore by the fact that the clamping holder is lined up on the tensioning rod, comprising a through-opening which is designed in such a way that the tensioning rod passes through the through-opening with sufficient play in the through-opening for spatial guidance of the clamping holder. A number of advantages are gained with the solution of the invention. Due to the three-dimensional guiding of movement and capacity of the clamping holder for displacement, adjustment and connection of the fixation element to fixation rods is particularly simplified and facilitated. Also, this contributes to a particular extent to the rod and base body or clamping bearing not being braced with forces transverse to the tensioning rod in the state of force-locking connection. This increases the strength and stability of the device to a particular extent. With regard to a simple shape, it is particularly advantageous that the clamping holder for the clamping rod forms a bearing which as such is movable as a unit in three dimensions, that is, in all spatial directions. The tensioning rod connection is particularly simple because portions to be clamped including the clamping holder which is guided and displaceable on the base body in all spatial directions are released by one and the same pull rod of the tensioning connection and attached to each other in a rigid connection. Tensioning force is applied uniformly to different parts of the tensioning combination, namely both for fixing the fixation rod in its clamping holder and for fixing the clamping holder of which the angle is spatially adjustable in a bearing element on the base body. The shape of connection and construction according to the invention allows the components to be made relatively simple. The manufacturing costs of the component parts remain low. Compared with traditional devices, the expenditure for component parts is considerably reduced with respect to number, handling and use. In particular, parts to be made by shape cutting chipping technology are avoided, and lightweight components preferably consisting of plastic injection mouldings are used instead.

A fixation element according to the invention which is particularly universally usable is achieved by the fact that on the tensioning rod are placed in a row at least one base body and on the base body opposite each other two rod clamping holders with their bearing portions. Appropriately, with this design the base body is formed by a cross-shaped element including a cylindrical longitudinal body portion which comprises bearing surfaces at its ends for a clamping holder each, and a transverse body portion which receives at least one bone nail. This shape of the base body, of which the longitudinal body portion has the tensioning rod passing through it, has relatively large resistance cross-sections for compression and/or bending loads, so that the tensioning connection is particularly firm and stable. Appropriately, along the extent of the transverse body portion in the latter is formed a through-slot which receives bone nails in regions of the transverse body portion projecting from the longitudinal body portion. This leads both to a spatially particularly favourable arrangement of the bone nails and a particularly effective and pronounced transmission of tensioning force along the longitudinal body portion. Also the result is that tightening for tensioning the connection is associated with only a relatively low tightening torque.

Due to the measures according to the invention, a fixation element including the base body and at least one rod clamping holder held thereon by means of the tensioning rod connection can be handled particularly easily and placed on appropriately two bone nails as a compact part joined together in a simple combination by itself.

Advantageously, the tensioning rod connection is formed by a screw/shank connection. This appropriately comprises two screws with a longitudinal shank which are screwed to each other in a passage in the base body, so that a tensioning rod which works by shortening is formed already by a few turns of the two screws relative to each other. The portions which are thus clamped are subjected to clamping pressure uniformly in a straight line. Instead, for example a continuous tensioning rod, which at least one end ends in a screw connection with a nut that can be tightened, can be used.

One particular design of the invention consists in that the tensioning rod connection, in addition to its function for fixing the rod holder and the rod, forms a tensioning means which in the released connection state lets at least one bone nail movably engage in a base body which is manufactured in one piece preferably from lightweight material such as plastic, while it fixes the bone nail to the base body in a non-positive locking stable relationship in the non-positive locking connection state.

Advantageously, in the base body is formed at least one slot for adjustably receiving and fastening a bone nail by clamping, the base body being elastically deformed in the region of the slot upon tensioning the tensioning rod connection. Appropriately, the slot in the base body and at least one bone nail received by it are given dimensions such that in the released state of the tensioning rod connection the bone nail is received by the slot in a clamping/sliding fit for adjusting the connecting position between bone nail and base body. In this embodiment the base body can be mounted particularly easily and reliably on bone nails.

According to the invention the rod clamping holder can advantageously be designed as an independent clamping element which in the released state of the tensioning rod connection receives at least one fixation rod in a press fit. Particularly advantageously, the clamping holder can be designed as an independently acting clamping element which receives the fixation rod in an elastic press fit due to the materials. The fixation rod can be moved at least in the axial direction against static friction for positioning. Also the rod clamping holder can appropriately be designed in such a way that the receptacle for the fixation rod comprises an opening through which the rod passes in the released state of the tensioning rod connection into a fit produced by at least one displaceable latch element. This facilitates handling substantially, as the fixation rod due to this measure is put in a position for adjustment by a click connection. Escape of the rod in the direction of insertion is prevented by this means. Nevertheless it remains movable in at least one dimension for adjustment.

In a further, particularly preferred embodiment of the invention, the three-dimensionally movable rod clamping holder comprises at least two through-openings, wherein a first opening is formed by a central axial through-opening through which the tensioning rod of the tensioning rod connection is passed, leaving sufficient radial play for the three-dimensional movement, and at least one second opening passes through the holder transversely to the axial opening and without intersecting the latter and forms the clamping receptacle for the fixation rod.

Appropriately, the holder which is guided three-dimensionally on the base body comprises spherical surface sections with which it is mounted in positive engagement between annular bearing elements in a row on the tensioning rod of the tensioning rod connection, wherein one bearing element is arranged on the base body which is held on the tensioning rod. A particularly advantageous measure consists in that the central through-opening of the clamping holder is expanded in the region of at least one spherical surface of the bearing in order to provide a spherical holder displacement region which is limited thereby. To keep the number of components particularly low, the clamping holder is appropriately formed by a one-piece ball. Advantageously, such a holder is designed with a rod clamping receptacle which on the holder surface forms an open slot for receiving the fixation rod.

In order to particularly strengthen the non-positive locking connection, a measure according to the invention consists in that at least one portion of the clamping surfaces of the fixation device is structured. Appropriately, the structuring comprises roughening, grooves, knobs and/or a corresponding means for producing particularly intimate engagement.

Due to the measures according to the invention, a relatively small number of components which can be kept ready in particular as cheap lightweight components in the form of a compact kit in a sterile package is achieved.

BRIEF DESCRIPTION OF THE DRAWINGS

Further preferred features, embodiments and possibilities of the invention are apparent from subsidiary claims and the description. Particularly preferred practical examples are described in more detail with the aid of the drawings. The drawings show:

DETAILED DESCRIPTION

Figure 1:
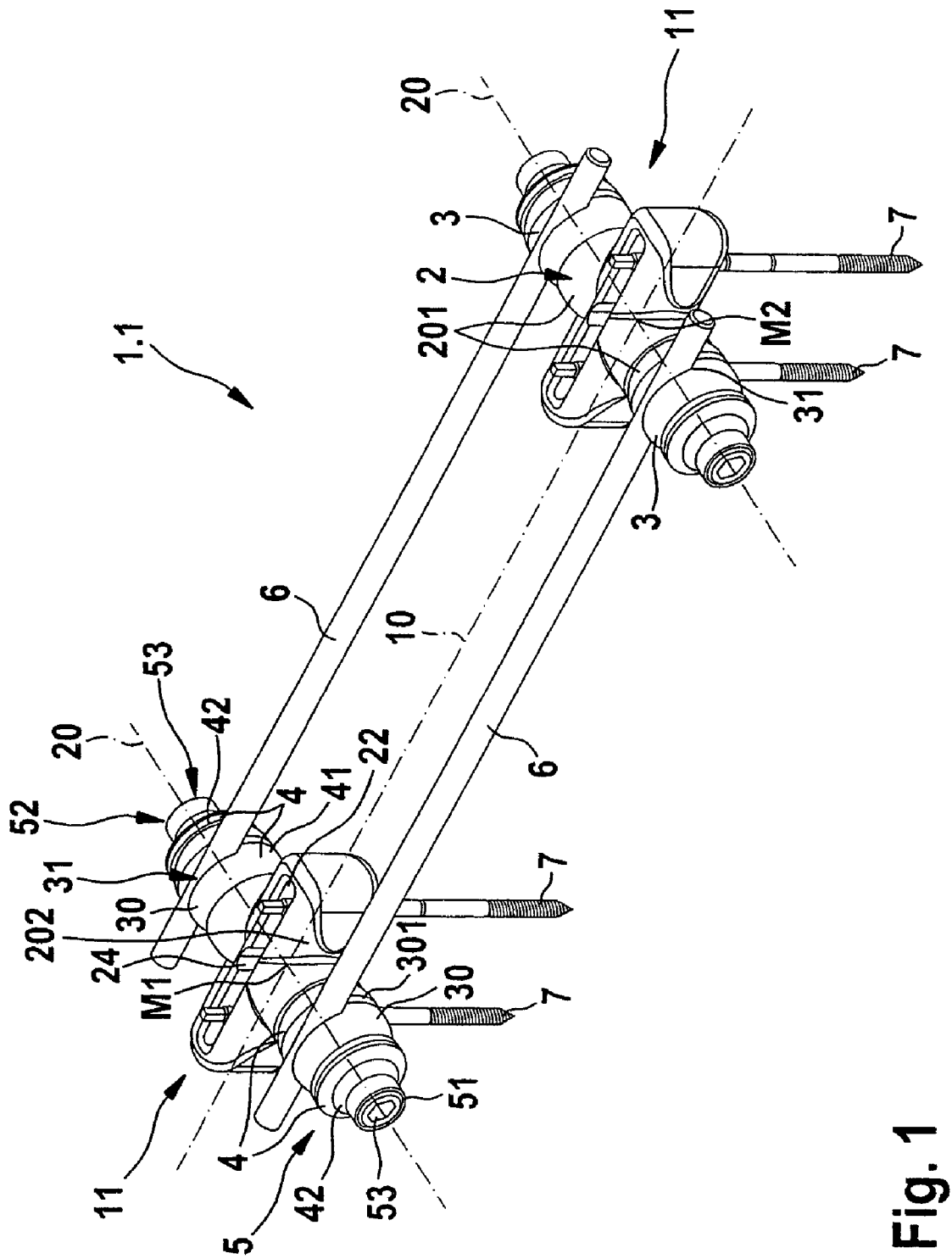
FIGS. 1 and 2 in an axonometric view and in an exploded view, a fixation device according to the invention with two fixation elements connected by two fixation rods, FIG. 3 in an axonometric view, a fixation device according to the invention with two fixation elements connected by only one fixation rod, and FIGS. 4 and 5 in an axonometric view and in an exploded view, a fixation device according to the invention with two connecting rods and two fixation elements which receive bone nails in a different arrangement.
Figure 2:
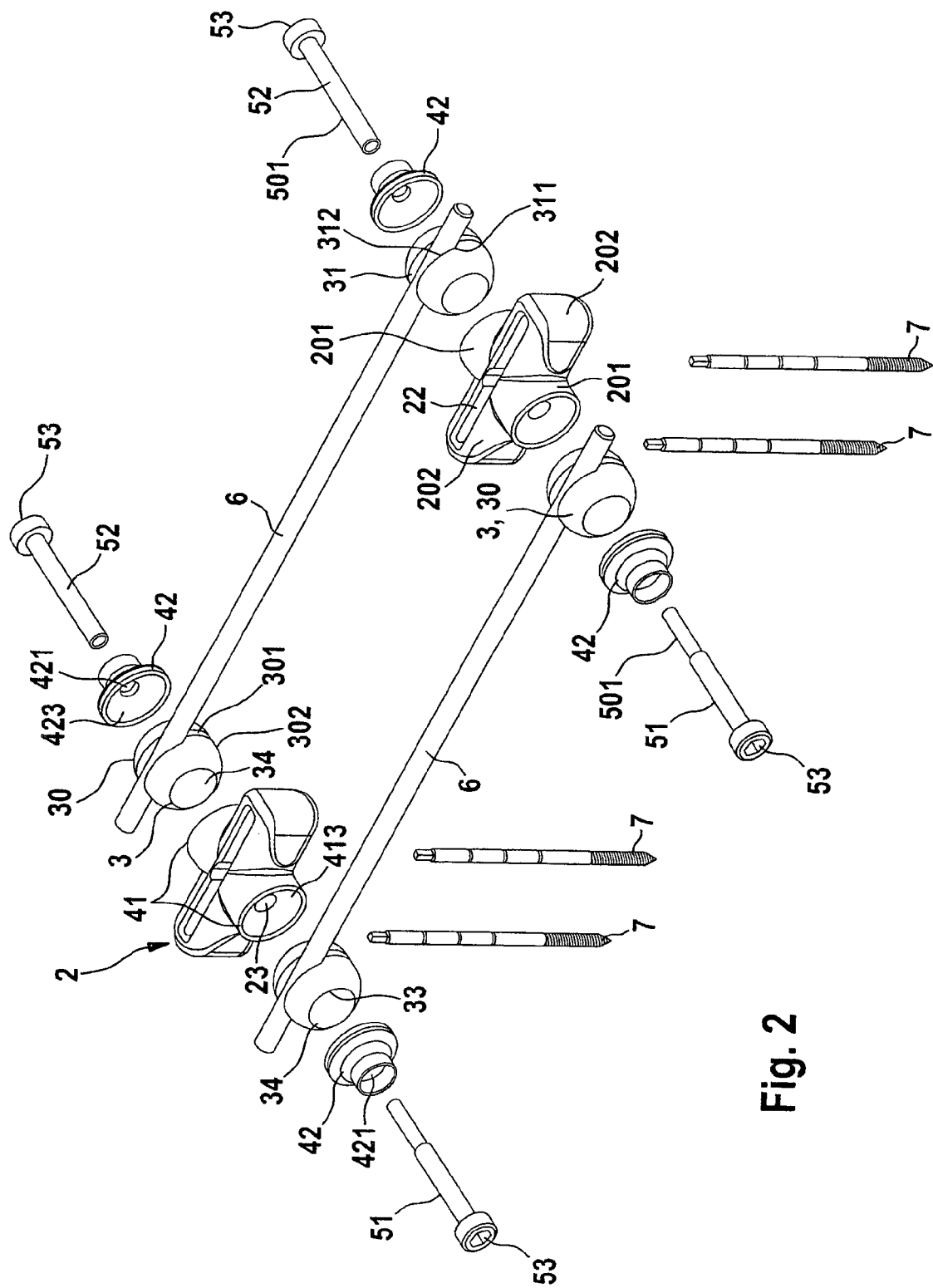

A first embodiment of a fixation device 1 according to the invention can be seen from FIGS. 1 and 2. This is composed of two fixation elements 11 according to the invention, bone nails 7 to which the elements 11 are applied, and two fixation rods 6. This is a fixator which with the two fixation rods 6 bridges a bone joint, e.g. a wrist, on the outside in order to make a fixation connection between broken bone portions. The fixation elements 11 are designed to match each other. The fixation rods 6 are shown in parallel alignment in FIGS. 1 and 2. But the device according to the invention allows them to be adjusted with a large deviation from parallel alignment as well. The bone nails 7 for the fixation element 11 each stand in a line which runs at least almost parallel to the fixation rods 6.

The fixation element 11 comprises a cross-shaped base body 2 which is made in one piece by a plastic part formed by injection moulding and to a certain extent is inherently deformable against the elastic return force of the materials for making clamping connections. For manufacture of the injection moulding, a high-strength plastic having a relatively low specific gravity is used. Such a body can be made with high precision with accurate shape and size.

The base body 2 which has a symmetrical cross shape is formed by a circular cylindrical longitudinal body portion 201 and a transverse body portion 202 which as a unit has an oval shape and with its ends projects perpendicularly from the cylinder body portion 201. The dimensions of the cross-sections of the portions 201 and 202 which are each perpendicular to the long direction in which they extend are of the same order of magnitude. In the transverse body portion 202 is formed a flat through-slot closed at the edges for forming a receptacle 22 for a pair of bone nails 7. The slot receptacle 22 extends with the transverse body portion 202, wherein the slot with its flat surface is perpendicular to the central longitudinal axis 20 of the longitudinal body portion 201 and open at free narrow sides of the transverse body portion 202 for placing on the bone nails 7. The longitudinal body portion 201 has an axial through-bore 23 through which is passed a tensioning rod 501 of a tensioning connection 5.

The fixation element 11 is formed as a unit by a captive arrangement in a row of the base body 2, two rod clamping holders 3 and clamping holder bearing elements 41, 42 of a bearing 4 on the tensioning rod 501. The rod clamping holders 3 enclose between them the base body 2, and this arrangement is encompassed in positive engagement with two bearing ring elements 42 in the form of calotte-shaped caps between their concave ring sides.

The two rod clamping holders 3 are designed to match each other. The clamping holder 3 is formed by a one-piece clamping ball 30 which has an axial central through-opening 33 in the form of a bore. The through-opening 33 merges with a concave annular recess 34 at each of its opening ends. Each ball 30 which is made of high-strength plastic is received in positive engagement by the bearing 4. Each bearing 4 has a bearing element 41 each formed at the end of the longitudinal body portion 201 in the form of a calotte-shaped recess 413 forming a concave bearing ring, and an associated bearing element 42. Each bearing element 42 has a through-hole 421 with which it is fitted on the tensioning rod 501 at the end of the latter. The bearing element 42 is formed, on its side facing towards the bearing ball 30, with a concave annular recess 423 which corresponds to the concave annular recess 413 of the bearing element 41.

The clamping holder bearing ball 30 is further designed with a slot receptacle 31 for receiving and holding the fixation rod 6. The slot receptacle 31 extends in a ball secant region in the equatorial plane of the ball without intersecting the axial through-opening 33 of the ball 30. The slot receptacle 31 is expanded at its bottom to match the circular cross-section of the fixation rod 6, forming a seat 311 through which the fixation rod 6 passes at its end. Furthermore, the walls of the slot 31 form latch elements 312 which are expandable against the elastic return force of the material in order to let the fixation rod 6 latch in the seat 311 in clamping relationship. The receiving cross-sections of the slot receptacle 31 and the material elasticity of the bearing ball 30 are selected such that the rod 6 is automatically held by clamping in the latched position, wherein it is movable axially and rotationally against clamping friction force for positioning and adjustment. Also, the bearing ball 30 in its equatorial plane is divided by a gap 301 into two halves which are held together in one piece by a wall web 302 only on the ball side opposite the slot receptacle 31. The gap 301 is formed by a notch. The one-piece bearing ball 30 can be handled particularly easily. Instead, it is also possible to make the ball halves completely separate from each other.

The through-opening 33 passes through the gap 302. As a result, the ball halves are tensioned relative to each other with a uniform and relatively small tensioning force of the tensioning rod connection 5 for fixing the rod 6 in the slot receptacle 31. The tensioning force exerted via the bearing elements 41, 42 in the process also clamps the bearing ball 30 between the bearing elements 41, 42, so that at the same time the ball 30 is fixed in position easily and very stably. The diameter of the bearing ball 30 is only slightly larger than the cross-sectional diameter of the cylindrical longitudinal body portion 203 and of the bearing element 42. Consequently, the bearing balls 30 form highly effective clamping elements in the arrangement in a row on the tensioning rod 501 when they are pulled towards each other by the tensioning rod 501.

The tensioning rod 501 of the tensioning connection 5 of each fixation element 11 is formed by set screws 51 and 52 which can be screwed axially to each other at their bottom ends. For this purpose set screw 51 is provided with an external thread at its bottom end, and set screw 52 is provided with an internal thread at its bottom end. The set screws 51, 52 have heads 53 each with an internal polygonal recess for applying a screwdriver. On the bearing elements 42 are formed, in each case on the side facing away from the bearing ball 30, recesses in which the screw heads 53 engage for tensioning the parts arranged in a row on the tensioning rod 501 relative to each other.

The bearing ball 30 of each clamping holder 3 is thus mounted in positive engagement between the bearing rings 41, 42 in such a way that it is guided and three-dimensionally displaceable in its seat in the bearing elements 41, 42 when the tensioning connection 5 is sufficiently undone. To obtain a sufficiently large and limited spherical displacement range, the axial through-opening 33 is given sufficiently large dimensions, and the concave annular recesses 34 are expanded outwardly in a cone shape from the opening 33.

Advantageously and appropriately, the displacement range is selected so large that, starting from the position shown in FIG. 1 in which the two base bodies 2 with the axes 20 of their longitudinal body portions 201 are aligned parallel in one plane, the longitudinal body portions 201 or their axes 20 when the rods 6 intersect with each other can be torsionally rotated or pivoted relative to each other by at least 90° about an imaginary unidirectional axis 10 comprising the centres M1 and M2 of the cross pieces. The two axes 20 can therefore be moved at least into a position perpendicular to each other. In the process the imaginary axis 10 is not fixed, but can be moved in all spatial directions out of the basic position shown in FIG. 1.

The slot 22 in each base body 2 and the identical bone nails 7 received by it in a pair have dimensions such that the bone nails 7 are received in clamping relationship against the elastic return force of the wall material of the base body 2 in a sliding fit even when the tensioning connection 5 is fully undone. On the slot 22 at the centre of the cross piece of the base body is formed a recess 24 oriented perpendicularly to the axial through-bore 23 and having a shape corresponding to the polygonal recess in the screw head 53. By inserting and turning the rotating tool with which the tensioning connection 5 is also tensioned, the slot 22 can be expanded slightly against the elastic return force of the material of the slot wall in order to place the fixation element 11 easily on the pair of bone nails. In the process the two bone nails 7 each come to lie in the slot region which extends in the ends of the transverse body portion 202 projecting from the longitudinal body portion 201. The arrangement of the bone nails 7 in the ends of the transverse body portion 202 which project from the longitudinal body portion 201 leads to particularly effective clamping in the tensioning combination according to the invention. As a result, the central region of the receiving slot 22 between the nails 7 is uniformly and markedly elastically pressure-deformable in the direction of the tensioning rod 501 during tensioning. Also, the shape of the parts of the base body cross piece paired with the plastic materials used forms optimally working cross-sections for permanently and stably tensioning the tensioning rod connection 5.

The surgical technique for applying the fixation device according to the invention proves to be particularly simple and reliable. After two pairs of bone nails 7 have been placed substantially in a line in the usual manner with screw-in tool and drilling jig, the fixation element 11 is fitted onto each pair of nails. A screwing tool is inserted in the recess 24 and turned into a position such that the slot 31 is expanded for fitting. In the turned-back position of the tool it is removed, and the fixation element sits sufficiently tight for adjusting by shifting its position, but slidably on the bone nails 7. After both fixation elements 11 have been applied to the associated bone nails 7, the two fixation rods 6 are inserted. The bearing balls 30 are open with their slot recesses 31 on the side which faces away from the bone portions to be joined, and they can easily be displaced three-dimensionally into lockable positions for inserting and displacing the rods 6. In the process the rods 6 first pass with their ends into captive click-latch positions in which they remain displaceably for adjustment by the fact that they are movable on the one hand axially and rotationally by the automatic clamping action of the elastic clamping ball 30 and on the other hand by spherical displacement of the ball 30 in the bearing 4. With the capacity for universal displacement for adjustment combined in one unit according to the invention, the two fixation rods 6 are kept largely tension-free in relation to each other. Here it is highly advantageous that both the bone nails 7 and the fixation rods 6 are displaceable for adjustment by the automatic clamping action in the slot receptacle 22 of the base body 2 and in the slot receptacle 31 of the bearing ball 30 without affecting the tensioning connection 5. But also it is possible to tighten the tensioning rod connections 5 slightly in order to superimpose an additional component for adjustment on the inherent clamping actions. For fully fixing the parts relative to each other, the tensioning rod connection 5 is tensioned by tightening and tensioning the tensioning rod 501 to a given torque. This is achieved according to the invention by the fact that all clamping actions on the fixation element 11 are accomplished uniformly with only the one tensioning rod connection 5.

Figure 3:
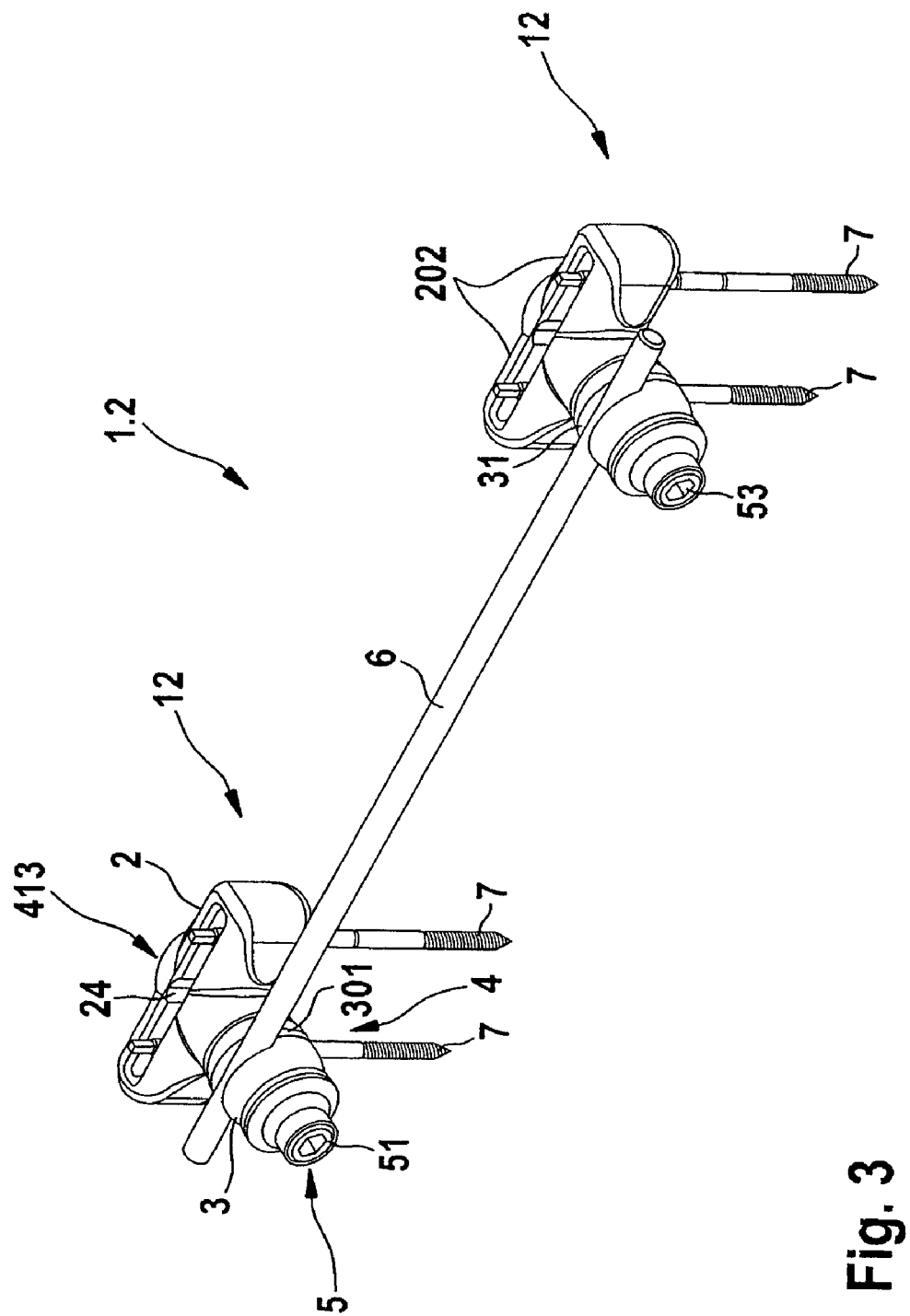

In FIG. 3 can be seen a fixation device 1.2 according to the invention, which is assembled from the same components as the fixation device 1.1 of FIGS. 1 and 2. Fixation elements 12 of this arrangement are formed by the fact that the base body 2 and the rod clamping holder 3 are placed on the tensioning rod at only one end of the cylindrical longitudinal body 201. On the other side the recess 413 in the bearing element 41 serves to receive the screw head 53. Appropriately, a tensioning rod 501 with screw elements 51, 52 is used, which allow the tensioning length to be altered within a wide range, in order to be used both for the device as in FIGS. 1 and 2 and for the device as in FIG. 3.

Figure 4:
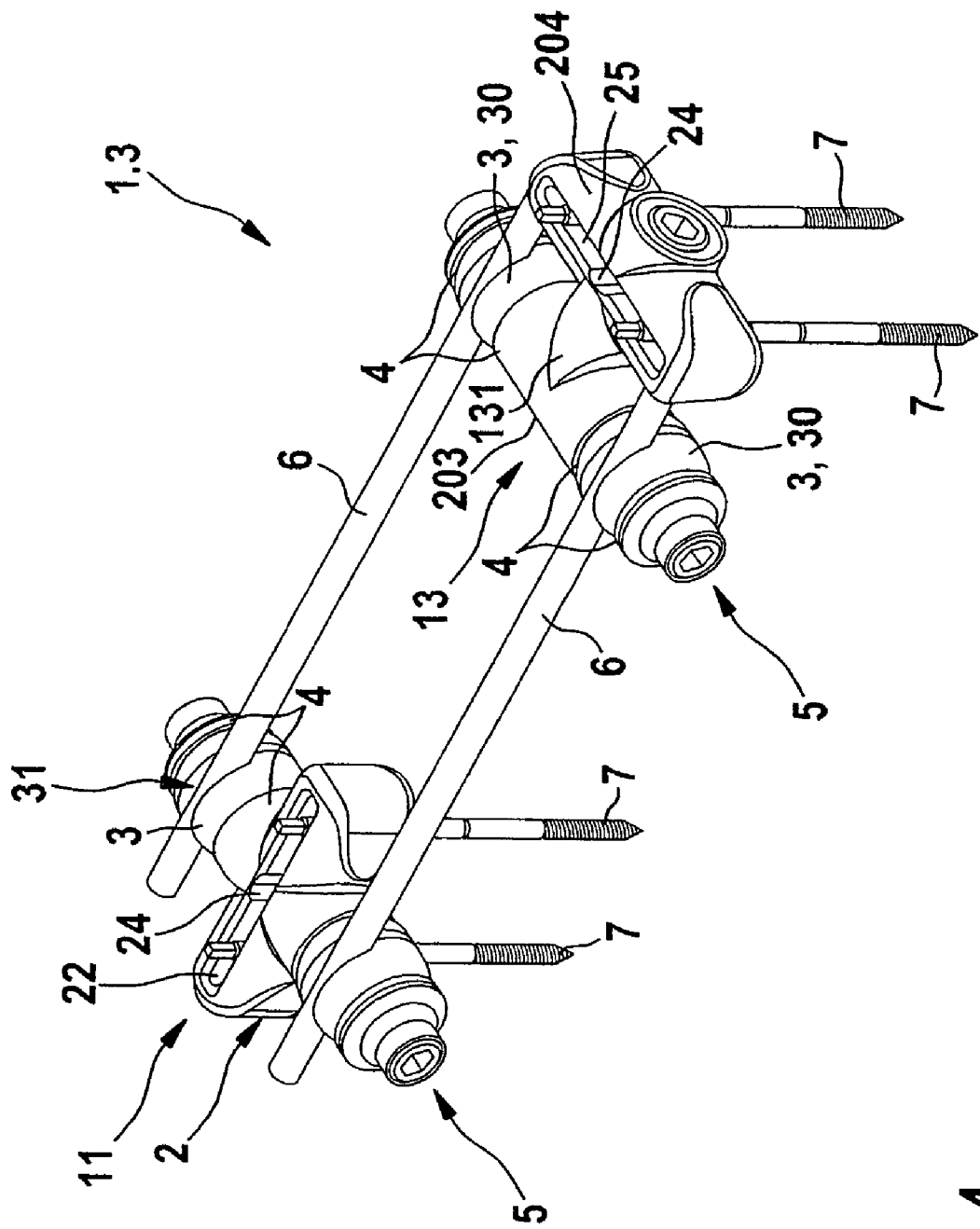
Figure 5:
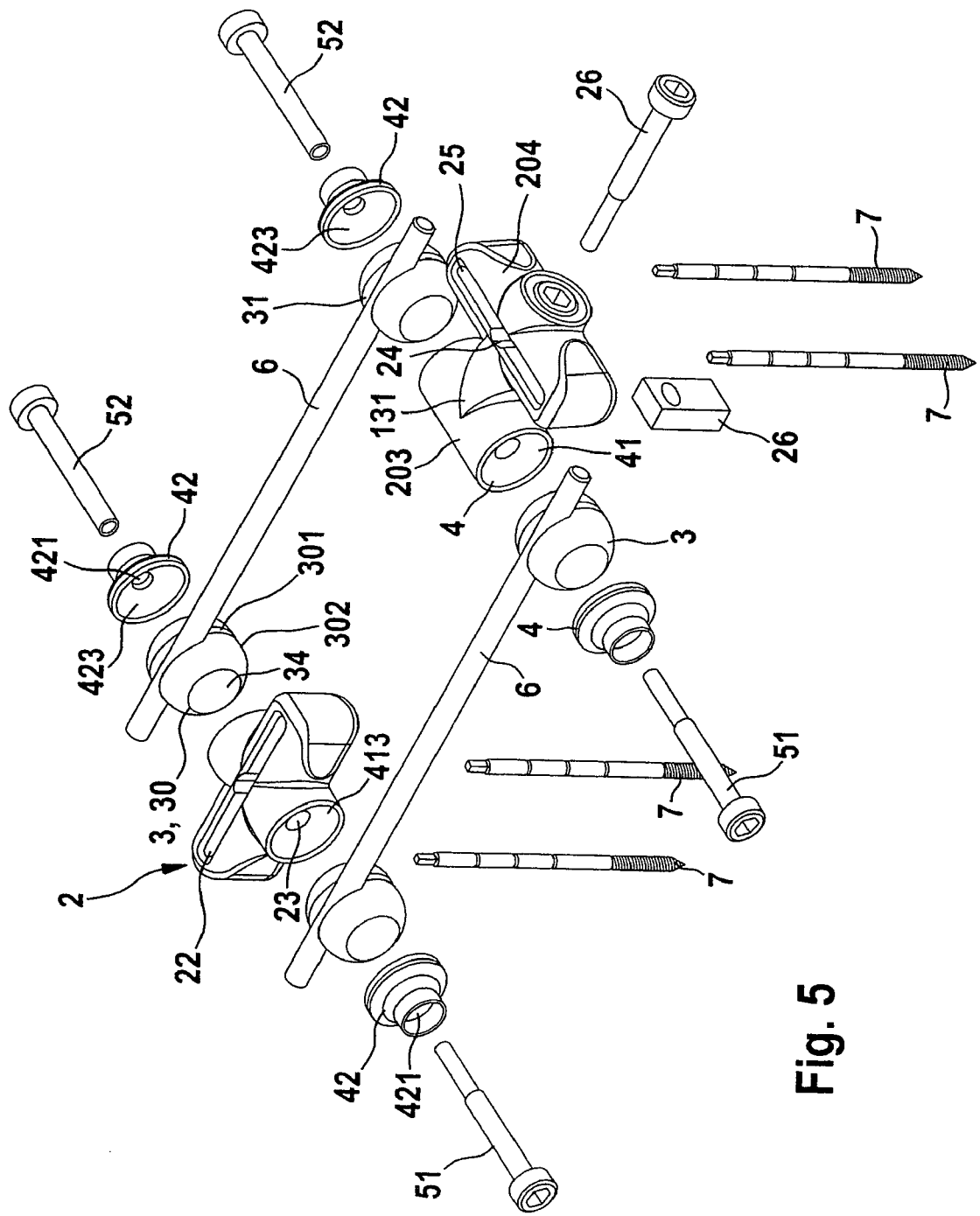

FIGS. 4 and 5 show a fixation device 1.3 according to the invention in an embodiment having a modified fixation element 13.

At one end of the arrangement of the fixation rods 6 extending substantially parallel to each other is arranged the fixation element 11, as described for FIGS. 1 and 2 The fixation rods 6 are connected at their other ends to the modified fixation element 13. The latter is designed like the fixation element 11, with the exception that, instead of the longitudinal body portion 201, there is provided a longitudinal body portion 203 which remains free from a transverse portion and is instead provided with an additional oval longitudinal body portion 204. The latter extends parallel to the body portion 203 to which it is connected by an attachment piece 131. In the body portion 204 in the direction in which it extends is formed a slot receptacle 25 for a pair of bone nails 7. The design of this slot with tool recess 24 corresponds to the design of the slot in the portion 202 of the other fixation element 11. As can be seen from FIGS. 4 and 5, the fixation element 13 serves to receive a pair of bone nails 7 which stand transversely, in particular at least almost in a line perpendicular to the rods 6.

In the practical example of FIGS. 4 and 5, the body portion 204 has been made separate and connected by a screw connection 26 to the attachment piece 131 formed integrally on the body 203. The screw connection 26 is also used to fix the bone nails 7, as in the slot receptacle 22, in the slot receptacle 25.

The invention claimed is:

1. A fixation device to establish a stable connection of at least two bone portions of a broken bone, including:
   a base body to tightly receive a bone nail;
   a rod clamping holder having a clamping receptacle and a through-opening;
   a fixation rod receivable in the receptacle of the rod clamping holder;
   a bearing element configured to mount the rod clamping holder on the base body so that the rod clamping holder is spherically displaceable in the bearing element; and
   a tensioning rod connection including a tensioning rod on which the base body, the rod clamping holder and the bearing element are arrangeable in a row for tensioning relative to each other, wherein the tensioning rod connection has a first connection state when the tensioning rod connection is released so that the rod clamping holder together with the fixation rod are adjustable relative to the base body in all spatial directions, and a second connection state when there is sufficient closing tension in the tensioning rod connection to form a stable non-positive locking connection between the fixation rod and the base body to fix an adjusted relative position of the fixation rod and base body, and wherein in the first connection state the rod clamping holder and the bearing element are in positive engagement and the tensioning rod passes through the through-opening of the rod clamping holder with sufficient play in the through-opening to permit spherical displacement in all directions of the rod clamping holder.

2. The fixation device according to claim 1, wherein the base body is formed in one piece and the base body, the rod clamping holder and the bearing element each are placed in a row on the tensioning rod.

3. The fixation device according to claim 1, wherein the bearing element comprises two bearing elements located on opposite sides of the base body, and said rod clamping holder comprises two rod clamping holders on opposite sides of the base body mounted in a respective one of the bearing elements, and the base body, bearing elements and rod clamping holders are placed in a row on the tension rod.

4. The fixation device according to claim 1, wherein the tensioning rod Connection is formed by a screw/shank connection.

5. The fixation device according to claim 1, wherein the through-opening through which the tensioning rod of the tensioning rod connection is passed has a central axis that is coincident with a central axis of the rod clamping holder and leaves, sufficient radial play for a three-dimensional movement of the tensioning rod, and wherein the clamping receptacle passes through the rod clamping holder transversely to the through-opening and without intersecting the through-opening.

6. The fixation device according to claim 5, wherein the bearing comprises annular bearing elements and the rod clamping holder comprises spherical surface sections with which the rod clamping holder is mounted in positive engagement between the annular bearing elements in a row on the tensioning rod, wherein one bearing element is arranged on the base body and forms one piece with the base body.

7. The fixation device according to claim 6, wherein the bearing elements have spherical surfaces and the central through-opening of the holder includes an expansion in a region of at least one spherical surface of the bearing element in order to provide a spherical holder displacement region which is limited thereby.

8. The fixation device according to claim 6, wherein the rod clamping holder comprises a one-part or two-part ball.

9. The fixation device according to claim 6, wherein the rod clamping holder is one piece and the clamping receptacle for the fixation rod comprises an open receiving slot on a surface of the rod clamping holder.

10. The fixation device according to claim 1, wherein the tensioning rod connection in the first state allows at least one bone nail to be movably engaged in the base body and in the second state fixes the bone nail to the base body in a non-positive locking stable relationship.

11. The fixation device according to claim 10, wherein the base body includes at least one slot for adjustably receiving and fastening the bone nail by clamping, the base body being elastically deformed in the region of the slot upon tensioning the tensioning rod connection.

12. The fixation device according to claim 11, wherein the slot in the base body and the bone nail received by the slot are dimensioned such that in the first connection state of the tensioning rod connection the bone nail is received by the slot in a clamping/sliding fit for adjusting the connecting position between the bone nail and base body.

13. The fixation device according to claim 12, wherein the slot has a wall of elastic material such that the slot cross-section can be expanded for introducing the bone nail against a return force by of a tool.

14. The fixation device according to claim 13, wherein the wall of the slot in the base body includes a recess for applying a tool for elastic expansion of the slot.

15. The fixation device according to claim 13, wherein the tensioning rod connection has a shaped recess for engagement by a tool for tensioning and relaxing the tensioning rod connection, which can be actuated with the tool for expansion of the slot in the base body.

16. The fixation device according to claim 1, wherein the rod clamping holder comprises an elastic material, and wherein in the first state of the tensioning rod connection, the fixation rod is held in a press fit in the receptacle of the rod clamping holder which independently holds and clamps the fixation rod due to the elasticity of the material, and wherein the fixation rod in the press fit is movable at least in an axial direction for positioning.

17. The fixation device according to claim 1, wherein the rod clamping holder includes at least one displaceable latch element adjacent an opening of the receptacle of the rod clamping holder, and in the first state of the tensioning rod connection, the fixation rod passes through the receptacle opening to form a press-a fit produced by the at least one displaceable latch element.

18. The fixation device according to claim 1, wherein the base body includes at least one receptacle which receives at least two bone nails arranged in a row along the direction in which a fixation rod extends.

19. The fixation device according to claim 1, wherein the base body includes at least one slot arranged to receive at least two bone nails arranged in a row transversely to the direction in which the fixation rod extends.

20. The fixation device according to claim 1, wherein at least one portion of clamping surfaces of the fixation device includes structuring formed by roughening, grooves, knobs or the like, to strengthen the non-positive locking connection.

21. The fixation device according to claim 1, wherein the bearing element includes two bearing elements with bearing surfaces and the base body comprises a cross-shaped element having a cylindrical longitudinal body portion including the bearing surfaces of the bearing elements at its ends to receive, respectively, a said clamping holder each, and having a transverse body portion with regions projecting from the cylindrical longitudinal body portion, the transverse body portion having through-slots in the projecting regions each for receiving at least one bone nail.

22. The fixation device according to claim 21, wherein the transverse body portion has an oval shape with rounded surfaces.

23. The fixation device according to claim 1, wherein the bearing element includes two bearing elements with bearing surfaces, and the base body comprises a cylindrical longitudinal body portion including the bearing surfaces of the bearing elements at its ends to receive, respectively, a said clamping holder, and wherein the base body further includes a receiving body rigidly connected to and extending parallel to the longitudinal body and having at least one through-slot for receiving at least one bone nail.

24. A fixation element as embodied in the fixation device according to claim 1, including the base body and at least one rod clamping holder held thereon by the tensioning rod connection.

25. A kit in a sterile package for surgical assembly of a fixation device to establish a stable connection of at least two bone portions of a broken bone, the kit including:
- a base body to tightly receive a bone nail, the base body including a bearing element;
- a rod clamping holder having a clamping receptacle and a through-opening;
- a fixation rod receivable in the receptacle of the rod clamping holder;
- a bearing element configured to mount the rod clamping holder on the base body so that the rod clamping holder is spherically displaceable in the bearing element; and
- a tensioning rod connection including a tensioning rod on which the base body, the rod clamping holder and the bearing element for the clamping holder are arrangeable in a row for tensioning relative to each other, wherein the tensioning rod connection has a first connection state when the tensioning rod connection is released so that the fixation rod and base body are adjustable relative to each other, and a second connection state when there is sufficient closing tension in the tensioning rod connection to form a stable non-positive locking connection between the fixation rod and the base body, wherein the rod clamping holder and the bearing element are in positive engagement in the first connection state with the tensioning rod passing through the through-opening of the rod clamping holder with sufficient play in the through-opening for spatial guiding in all directions of the fixation rod by the rod clamping holder.

* * * * *